United States Patent [19]

Smith

[11] 4,305,968

[45] Dec. 15, 1981

[54] MODIFICATION OF BIOLOGICAL ACTION OF SACCHARIN

[76] Inventor: Walton J. Smith, U.S. Rte. 4, Grafton, N.H. 03240

[21] Appl. No.: 73,796

[22] Filed: Sep. 10, 1979

Related U.S. Application Data

[63] Continuation of Ser. No. 852,327, Nov. 17, 1977, abandoned.

[51] Int. Cl.³ .......................................... C07D 231/54
[52] U.S. Cl. .................................. 426/548; 548/211; 426/656
[58] Field of Search ....................... 548/211; 426/548; 71/91, 77

[56] References Cited

U.S. PATENT DOCUMENTS 3,325,475  6/1967  Vacek ................................. 260/211
3,717,477  2/1973  Nonomiya ........................... 426/548

FOREIGN PATENT DOCUMENTS 1217392  5/1966  Fed. Rep. of Germany .
1225653  9/1966  Fed. Rep. of Germany .

*Primary Examiner*—Nicholas S. Rizzo
*Attorney, Agent, or Firm*—Larson and Taylor

[57] ABSTRACT

Members of the urea cycle, i.e. urea, ornithine, arginine and citrulline have been found to reduce the toxicity of saccharin.

2 Claims, No Drawings

MODIFICATION OF BIOLOGICAL ACTION OF SACCHARIN

This is a continuation of application Ser. No. 852,327 filed Nov. 17, 1977, now abandoned.

This invention pertains to methods and products relating to the reduction in toxicity to biological systems due to saccharin and its salts.

The effect of saccharin in animals and humans other than its taste effects has not been completely clarified. It is believed to increase the tendency toward abnormal growths in rats when fed at high levels, and possibly at lower levels. Recent controversial studies implicate saccharin as a carcinogen. It is relatively non-toxic to fish and animals in acute tests making precise studies very difficult.

I have found that it is somewhat toxic to plants as evidenced by growth inhibition, and I have chosen this area for my studies since it lends itself to very precise measurement of toxicity and the measurement of methods of overcoming this toxicity.

Because saccharin is more soluble as the salt than as the free acid, I have chosen to study it in salt form. Animal studies in which tumor formations have been observed, have also used saccharin salts. I have used the calcium salt for my studies because the cation, calcium, is known to be harmless to plants, and indeed is utilized by plants.

I have found that calcium saccharin inhibits the growth of a variety of plants including for example, cucumber, radish and wheat. This is manifested in reduced growth and at some levels death of the plant, thus demonstrating the toxicity of saccharin to cells.

I have discovered that I can counteract this growth inhibition by supplementing the medium with a member of the urea cycle, i.e., one or more substances selected from the group consisting of urea, ornithine, citrulline and arginine, which I will call a "saccharin antagonist". I have also discovered that a satisfactory level of use to achieve this objective is a quantity comparable to the quantity of saccharin salt present. At this level of use, I have found that the saccharin antagonist does not significantly detract from the taste advantages of the saccharin. Urea is of particular value in this respect. Because the antagonist is a normal body substance, it can be safely ingested by animals.

During the course of my extensive research, I have found a wide variety of other compounds which are present in metabolic pathways in the body to be ineffective as saccharin antagonists. Some examples of ineffective compounds are oxalacetic acid, sodium formate, malic acid, among many others. I have evaluated naturally occurring compounds included in carbohydrate metabolism, purine and pyrimidine metabolism, a variety of amino acid cycles, citric acid cycles, vitamins, etc. Thus, the action of the urea cycle compounds appears to be unique.

In specific experiments, I have found arginine to be effective in either the base or the salt form.

Preliminary experiments suggest that ornithine and citrulline are also effective. My work has been with the natural isomers.

Because it is inexpensive and relatively non-toxic, urea is the saccharin antagonist. Further, I have found the salt formed between the acid saccharin and urea to be especially convenient since this provides the desired quantitative relationship between the ingredients. I have also made a saccharin salt of 1-Arginine. Because saccharin in acid form is a fairly strong acid, the above two salts can be nicely characterized.

It is seen in the following example that urea is not totally non-toxic to plants, nor is it totally non-toxic in animals, though it is quite safe in small amounts in both plants and animals. For this reason, the quantity used for partial detoxification of the saccharin is held to as low a quantity as practical, and this is from about ½ part of urea per part of saccharin to an equal quantity, on a weight basis.

EXAMPLE 1

Balsam seeds were planted in vermiculite and grown in a nutrient medium containing calcium, potassium, magnesium, manganese, iron, as cations, and sulfate, phosphate, borate, nitrate as anions. This was the control solution to which was added calcium saccharin at a level of 0.3 mg/cc. In addition, the saccharin solution was supplemented in separate and simultaneous growth studies with urea at the same level. Additionally, a parallel study was made with urea but without saccharin. A similar and parallel study was made with calcium saccharin at 0.6 mg/cc and urea at the same level. A group of approximately twenty plants was used in each study. The test period was 27 days at approximately 75° F. average temperature under fluorescent lights. At the end of that period, the stem and leaf growth was measured by weighing the plants with the following results:

|  | Upper plant weight |
|---|---|
| Plant Nutrient Solution | 2.67 grams per plant |
| + Urea 0.6 mg/cc | 1.46 |
| + Ca Saccharin 0.3 mg/cc | 0.39 |
| + Urea 0.3 mg/cc | 0.53 |
| + Ca Saccharin 0.6 mg/cc | 0.36 |
| + Urea 0.6 mg/cc | 1.46 |

The figures are averages of the approximately twenty plants in each group.

EXAMPLE 2

Cucumber.

A similar study as the one described in Example 1 was made using cucumber in a 26 day study under identical conditions:

| Calcium Saccharin 0.3 mg/cc | 0.52 grams per plant |
|---|---|
| + Urea 0.3 mg/cc | 0.98 |
| Calcium Saccharin 0.6 mg/cc | 0.48 |
| + Urea 0.6 mg/cc | 0.56 |

These results show firstly that, as expected, urea reduces plant growth under these otherwise optimal conditions. However, with balsam seeds, calcium saccharin effects a much greater growth reduction, leading to a final weight which is less tha one-third of the urea-inhibited weight. Since urea can also inhibit growth, it might be expected that the addition of urea to the saccharin-containing medium would further inhibit growth. To the contrary, and surprisingly, the urea now acts as a growth promotor, and indeed, entirely eliminates the inhibition due to saccharin when used at 0.6 gm/cc. A comparable effect is found with cucumbers.

I claim:

1. A composition consisting essentially of saccharin together with from ½ to 1 part by weight of a saccharin antagonist selected from the group consisting of urea, arginine, ornithine, and citrulline.

2. A composition consisting essentially of a salt of saccharin in acid form and a saccharin antagonist selected from arginine or urea.

* * * * *